United States Patent
Den Hartog et al.

(10) Patent No.: US 10,559,082 B2
(45) Date of Patent: Feb. 11, 2020

(54) ITERATIVE DIGITAL SUBTRACTION IMAGING FRO EMOBLIZATION PROCEDURES

(71) Applicant: KONINKLIJKE PHILIPS N.V., Eindhoven (NL)

(72) Inventors: Markus Johannes Harmen Den Hartog, Eindhoven (NL); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/541,910

(22) PCT Filed: Dec. 28, 2015

(86) PCT No.: PCT/EP2015/081256
§ 371 (c)(1),
(2) Date: Jul. 6, 2017

(87) PCT Pub. No.: WO2016/110422
PCT Pub. Date: Jul. 14, 2016

(65) Prior Publication Data
US 2018/0005379 A1 Jan. 4, 2018

(30) Foreign Application Priority Data

Jan. 7, 2015 (EP) ..................................... 15305009

(51) Int. Cl.
*G06K 9/00* (2006.01)
*G06T 7/00* (2017.01)
(Continued)

(52) U.S. Cl.
CPC ............ *G06T 7/0016* (2013.01); *A61B 6/487* (2013.01); *A61B 6/504* (2013.01); *G06T 5/004* (2013.01);
(Continued)

(58) Field of Classification Search
CPC ...... A61B 6/504; A61B 3/1241; G01R 33/56; G01R 33/563; G01R 33/5635;
(Continued)

(56) References Cited

U.S. PATENT DOCUMENTS

| 4,729,379 A | 3/1988 | Ohe |
| 7,551,721 B2 | 6/2009 | Nakaura |

(Continued)

OTHER PUBLICATIONS

Meijering, Erik H.W. et al "Retrospective Motion Correction in Digital Subtraction Angiography: A Review", IEEE Transactions on Medical Imaging, vol. 18, No. 1, Jan. 1999.

*Primary Examiner* — Avinash Yentrapati

(57) ABSTRACT

Method and related system (IPS) for visualizing in particular a volume of a substance during its deposition at a region of interest (ROI). A difference image is formed from a projection image and a mask image. The difference image is then analyzed to derive more accurate motion information about a motion or shape of the substance. The method or system (IPS) is capable of operating in an iterative manner. The proposed system and method can be used for processing fluoroscopic X-ray frame acquired by an imaging arrangement (100) during an embolization procedure.

10 Claims, 2 Drawing Sheets

(51) Int. Cl.
  *G06T 5/50*   (2006.01)
  *A61B 6/00*   (2006.01)
  *G06T 5/00*   (2006.01)

(52) U.S. Cl.
  CPC ...... *G06T 5/50* (2013.01); *G06T 2207/10121* (2013.01); *G06T 2207/20201* (2013.01); *G06T 2207/20224* (2013.01); *G06T 2207/30104* (2013.01)

(58) Field of Classification Search
  CPC . G06T 2207/30101; G06T 2207/30104; G06T 2211/404
  See application file for complete search history.

(56) References Cited

U.S. PATENT DOCUMENTS

| | | | |
|---|---|---|---|
| 8,553,963 B2 | 10/2013 | Rauch | |
| 2007/0195932 A1 | 8/2007 | Nakaura | |
| 2008/0051648 A1 | 2/2008 | Suri | |
| 2008/0101670 A1 | 5/2008 | Baumgart | |
| 2009/0310825 A1 | 12/2009 | Bontus | |
| 2010/0092061 A1* | 4/2010 | Chen | G06T 5/50 382/132 |
| 2010/0172474 A1* | 7/2010 | Vogt | G06T 5/50 378/98.12 |
| 2010/0329526 A1* | 12/2010 | Pfister | A61B 6/487 382/130 |
| 2011/0206257 A1 | 8/2011 | Qanadli | |
| 2013/0190615 A1 | 7/2013 | Royalty | |
| 2013/0345559 A1* | 12/2013 | Haemmerich | A61B 5/0275 600/431 |
| 2017/0340301 A1* | 11/2017 | Den Hartog | A61B 6/481 |
| 2017/0345145 A1* | 11/2017 | Nempont | G06T 7/246 |

* cited by examiner

ITERATIVE DIGITAL SUBTRACTION IMAGING FRO EMOBLIZATION PROCEDURES

CROSS-REFERNCE TO PRIOR APPLICATIONS

This application is the U.S. National Phase application under 35 U.S.C. § 371 of international Application No. PCT/EP2015/081256, filed on Dec. 28, 2015, which claims the benefit of European Patent Application No. 15305009.1, filed on Jan. 7, 2015. These applications are hereby incorporated by reference herein.

FIELD OF THE INVENTION

The invention relates to an image processing system, to an image processing method, to a computer program element and to a computer readable medium.

BACKGROUND OF THE INVENTION

In moving tissues, undergoing complex motion patterns, it is often challenging to visualize relatively small contrasts in X-ray fluoroscopy images. The situation can arise during imaging in embolization procedures where an embolization agent is deposited at a region of interest inside a patient.

A more specific example is a liver intervention, where the motions of the ribcage, heart, diaphragm and/or bowels combine to cause examples of such complex motion patterns. An additional factor that makes X-ray imaging challenging is that the transparency images created in X-ray usually feature several superimposed motion layers.

Sometimes subtraction imaging techniques are used to enhance the (image) contrast visibility but motions remain still a concern. A common subtraction based technique that uses contrast agents for visualizing is called DSA (Digital Subtraction Angiography). A refined example of this technique developed for cardiac interventions can be found in U.S. Pat. No. 4,729,379.

However, due to the very low contrast of the embolization material, the presence of in particular non-rigid movements of the tissue in embolization interventions (in particular, but not only, abdominal embolization) and the abundance of background tissue, visualization remains a challenge and known DSA techniques appear not to yield satisfactory imaging results.

SUMMARY OF THE INVENTION

The may be a need in the art for an alternative method and/or a related system to aid imaging of a deposition of a substance subject to motion.

The object of the present invention is solved by the subject matter of the independent claims where further embodiments are incorporated in the dependent claims. It should be noted that the following described aspect of the invention equally applies to the image processing method, to the computer program element and to the computer readable medium.

According to a first aspect of the invention there is provided an image processing system, comprising the following components:

an input port configured to receive i) a projection image acquired of a region of interest, ROI, in a specimen whilst a substance is present at or around said ROI and ii) a mask image, the mask image acquired at a different instant than the projection image when less of said substance is present, an amount of said substance capable of building up over time;

ROI focused motion compensator that operates to register the mask image and the projection image to motion compensate for a motion of the ROI;

a subtractor configured to subtract, after said image registration, the mask image from the projection image to obtain a difference image;

a motion estimator configured to estimate a motion of the ROI based on the difference image and based on i) the projection image or ii) the mask image; and an update module configured to input said estimated motion into at least one of the components and/or configured to adjust at least one of: the projection image or a subsequent projection image or the mask image or a subsequent mask image.

It is envisaged that the mask image and the projection image represent the ROI at different contrasts. In particular, the mask image is a further projection image acquired at a time before any substance was deposited at the ROI. According to one embodiment the motion compensation and/or subtraction is repeated based on the adjusted projection image or the adjusted mask image.

According to one embodiment, the motion compensator includes a landmark identifier configured to identify in the images a landmark that corresponds to the ROI or to a device resident in the specimen during imaging, in particular the device operative to deposit said substance.

According to one embodiment, the image processing system includes an image enhancer configured to filter the difference image for an image portion that represents the ROI.

According to one embodiment, the motion estimator uses the filtered difference image for the motion estimation.

According to one embodiment, the update module is configured to provide the estimated motion as input to the motion compensator or to the image enhancer module. The update module furnishes the estimated motion as "fresh" evidence about the motion and inputs same into a respective algorithm used by at least one of said components. For instance, it is envisaged to use the difference-image-based motion estimate as prior knowledge or as a constraint or as other input data in the respective algorithm(s) of the respective component.

According to one embodiment, the ROI is defined by the location and/or shape of the currently deposited substance.

According to one embodiment, the substance is a blob of embolization agent.

The proposed system can be used during tumor/AVM (Arteriovenous malformation) embolization procedures or other interventional X-ray procedures such as TACE (e.g., for liver). The difference images produced by the system afford improved visualization. The proposed system can be used in real-time visualization of embolization agent deposition, which is of particular benefit in AVM/tumor embolization procedures.

The proposed, new subtraction imaging technique takes advantage of a characteristic of embolization procedures where by, contrary to contrast agent injection as used in DSA, the embolic area builds up or accumulates relatively slowly, and remains in place.

This insight is taken advantage of by the present invention in that an initial, approximate subtraction result is used to enhance contrast of the embolized area as recorded at, say, time t. The enhancement then "focuses" on this area, using the enhanced difference image as "guidance" for subsequent subtraction refinement beyond time t, thus capturing the motion layer containing the targeted embolic material with relatively high accuracy. By construction, the proposed procedure can be used with particular benefit in an iterative setting, whereby the accuracy of the estimated motion of the embolized area further increases over time, resulting in higher quality subtraction images.

Among the advantages that the proposed system is able to secure is the ability to "focus" visualization on the deposited embolization agent at the region of interest (e.g., tumor site). This can be done in real time during the (essentially continuous) administration of the embolization material to better and more clearly capture the evolution of the embolus.

According to a second aspect there is provided an image processing method implemented by one or more components, comprising the steps of:

receiving i) a projection image acquired of a region of interest, ROI, in a specimen whilst a substance is present at or around said ROI and ii) a mask image, the mask projection image acquired at a different instant than the projection image when less of said substance is present, an amount of said substance capable of building up over time;

registering the mask image and the projection image to motion compensate for a motion of the ROI;

subtracting, after said image registration, the mask image from the projection image to obtain a difference image;

estimating a motion of the ROI based on the difference image and based on i) the projection image or ii) the mask image; and inputting said estimated motion into at least one of the components and/or adjusting at least one of: the projection image or a subsequent projection image or the mask image or a subsequent mask image.

According to one embodiment, the method comprises filtering the difference image for an image portion that represents the ROI.

According to one embodiment, the motion estimating step is based on the filtered difference image.

According to one embodiment, the motion compensation step and/or the subtraction step is repeated based on the adjusted projection image or the adjusted mask image.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
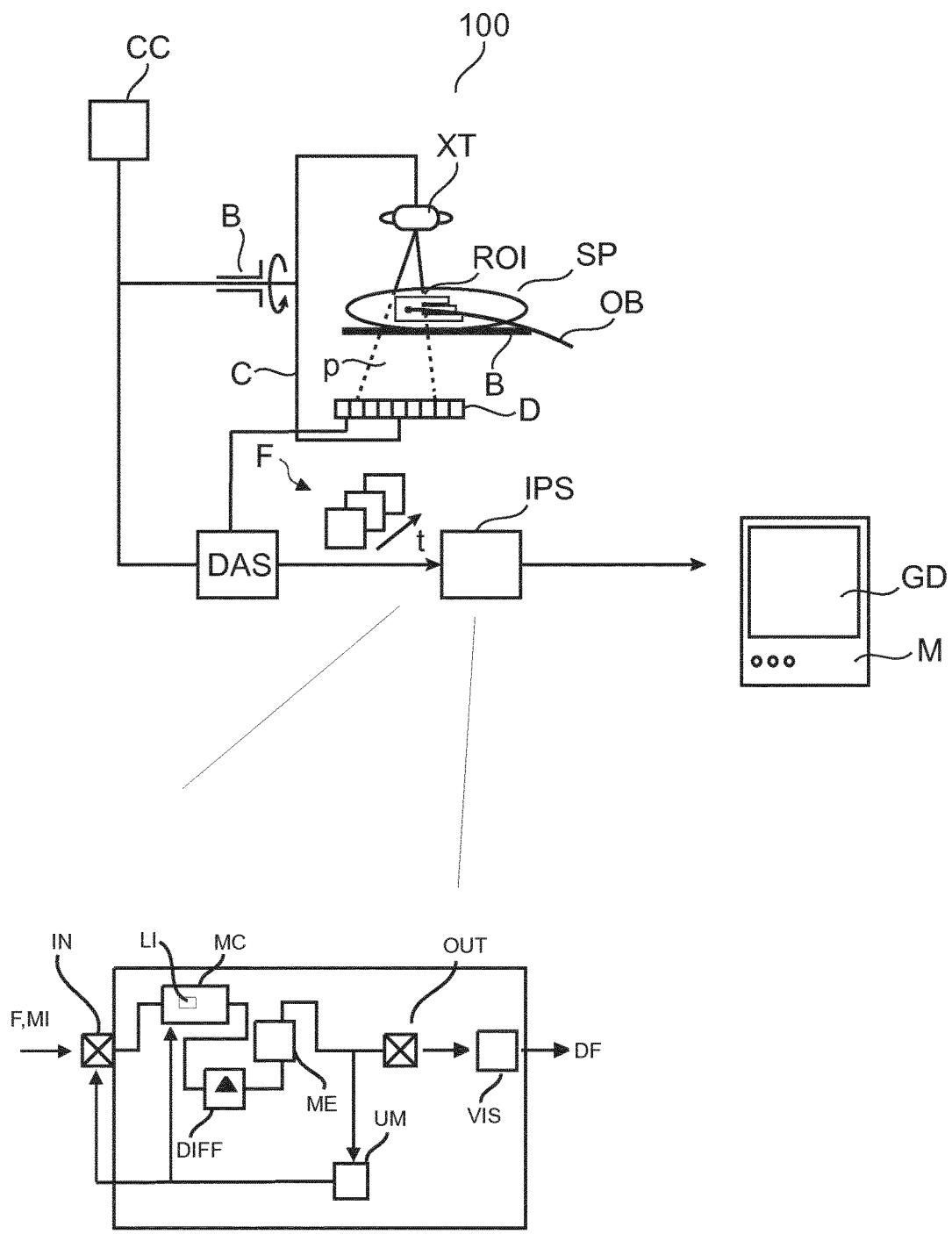
FIG. 1 shows an imaging arrangement.

With reference to FIG. 1, the components of a fluoroscopic imaging arrangement 100 are shown that can be used to support interventional procedures.

An example for such a procedure is trans-catheter arterial chemoembolization (TACE). To treat a liver tumor for instance, a catheter OB is introduced into the patient and advanced in general to a target vessel (such as the proper hepatic artery) that has been found to be a main feeder of the tumor. A volume or mass of embolization agent (hereinafter referred to as a "blob of glue", "embolus" or simply the "blob") is discharged through the catheter OB tip to occlude the vessel and to locally administer a chemotherapeutic drug that is included in the embolization agent as an admixture. The region of interest, ROI, where the deposition is to occur, is, for example, a portion of above mentioned hepatic artery or a shunt of a vessel that needs to be occluded because patient needs to undergo AVM (Arteriovenous Malformations), arteriovenous fistula (AVF), or Hemangioma treatment. Examples of liquid embolization materials are Onyx® (a glue-like substance), alcohol, or n-butyl cyanoacrylate (NBCA). Embolus administration commences at instant $t_0$ by releasing a volume of embolization agent via an open tip of said catheter near the ROI. Embolus then circulates in the bloodstream until it lodges in at a target position (e.g., a shunt linking the arterial to the venous systems), thereby occluding the blood vessel. During the deposition procedure, the embolus builds up gradually and, during at least parts of said deposition, a series of sequential fluoroscopic images F are acquired by an x-ray imager 100. During the intervention, patient SP is deposed on a bed B between an x-ray imager 100's x-ray tube XT and detector D. In one embodiment detector D is a component of an image intensifier that directly projects the imagery on a screen M for real-time observation. X-ray tube XT and detector D are attached to a rigid frame C rotatably mounted on a bearing B. The fluoroscopic image operation is controlled from a computer console CC. The interventional radiologist can control via said console CC image acquisition and can "shoot" a run of individual fluoroscopic frames ("fluoros") F by actuating a joy stick or a pedal. According to one embodiment, imager 100 is of the C-arm type but other systems are also envisaged.

During image acquisition, X-ray radiation emanates from x-ray tube XT, passes through the ROI, experiences attenuation by interaction with matter (including the embolus) therein, and the so attenuated beam p then strikes detector D's surface at one of plurality of detector pixels making up detector D. Each pixel that is struck by a beam responds by issuing a corresponding electrical signal. The collection of said signals is then translated into a respective digital value representative of said attenuation. The density of the material making up the ROI determines the level of attenuation with high density material causing higher attenuation than less denser materials. The so registered digital values for each x-ray p are then consolidated into an array of digital values forming a fluoro frame for a given acquisition time and projection direction. In other words each fluoro is a digital image of a projection view along a projection direction and said direction is determined by the rotation of the C-arm at the given acquisition time or instant. The series of fluoros F are then digitally processed by data acquisition unit DAS and are then forwarded to an image processer IPS whose purpose and operation will be explained in more detail below.

The stream of fluoroscopic frames F may comprise two types of frames depending on the relative timing of image acquisition and embolus deposition: the ones acquired without there being embolization agent present at the ROI, that is, frames acquired before commencement of the embolus deposition. These frames may be called "mask" frames. Instead of or in addition to those no-embolus frames, there are frames acquired whilst there is embolization agent present at the ROI. Those frames may be referred to herein as "contrast frames" of embolus frames. Alternatively, the mask image is acquired whilst there is some embolization agent present but the amount of embolization agent is less than when the embolus frame is acquired.

As will be explained in more details below, the frames are processed in a subtraction scheme to gather information about the embolization. For this purpose, the system further comprises the image processor IPS configured to act on the fluoroscopic image stream as furnished by the X-ray imager. The inset to the lower left of FIG. 1 shows details of the image processing system IPS as proposed herein.

The image processing system IPS as proposed herein implements a new subtraction imaging technique approach that takes advantage of a characteristic of embolization procedures where by, contrary to contrast agent injection, the embolic area builds up rather slowly, and remains in place. We propose to use initial approximate subtraction results to enhance the embolic area at time t, then to focus on this area, and use it as guidance for subsequent subtraction refinement at time t and beyond. By construction, the proposed procedure is naturally iterative although on occasion a "single" iteration may suffice. In other words, because the embolus remains present during the imaging and because an embolic-material-contrast-free mask frame is usually available (if image acquisition starts prior to the discharge of embolization at ROI), a first subtraction or difference image can be formed and used to bring forward a current state of embolization, which can then itself be used to focus on the motion layer containing this embolization area. One can then proceed iteratively: as the embolization carries on, and as the embolized area builds up, a projection footprint of the growing embolized area is then identified against background by a new subtraction and then used for further motion estimation, thus creating a natural embolization tracking mechanism.

The image processing system IPS as proposed herein includes an input port IN for receiving fluoroscopic frames from the stream of frames F supplied by the imager 100. Among the frames received is an embolus frame and a mask frame. The motion compensator MC operates to register the two images onto each other. For registration, only the motion of the region of interest is taken into account. The motion at the region of interest is established by tracking a footprint of the region of interest itself, in one embodiment this corresponds to the current footprint of the embolus or is established by looking at the footprint or landmark of other structures such as the tip of the catheter through which the embolus is discharged or other native or non-native structures whose motion is deterministically linked to that of the region of interest.

The so registered images are then subtracted from each other by a subtractor module DIFF. The difference image DF so formed may then be forwarded to output port OUT and made available for further processing such as, for instance, storage or visualization by means of a visualizer VIS on a screen MT. As proposed herein there is a feedback loop where the difference image itself is compared by a motion estimator with either the projection image or the mask image to re-establish the motion of the ROI, but now the difference image is used. This has the advantage that the motion information can be established more accurately because the embolus footprint is expected to show at higher contrast in the difference image. The motion estimator establishes motion information, for instance, a motion vector field in respect of the motion of the region of interest footprint only.

An updater module UM then feeds this motion information (for instance, said ROI focused motion vector field), into the motion compensator MC according to one embodiment. The above motion compensation can then be re-run now based on the new motion information as obtained by a motion estimator to derive a more accurate registration. The subtraction operation by subtractor DIFF can then be repeated to so derive at a new difference image that can be expected to be more accurate thus suffering from fewer artifacts than the initial subtraction which was merely an estimate. In this manner the above procedure can be repeated to iteratively improve the difference image.

In addition or instead, the update module UM may operate to adjust the projection image or mask image before they are fed into the motion compensator. Adjustment may include a pre-registration where the embolus image or the mask image is shifted according to the motion information so as to compensate or pre-compensate for the motion learnt by the motion estimator based on the previous (e.g., first or "initial") difference image from the previous registration. The above procedure may then be repeated in respect of a new current embolus frame and/or a new mask image as the motion compensator has been updated with respect to the motion as established by the motion estimation operation.

According to one embodiment the image processing system also includes an image enhancer IE, e.g., a filter module that operates on the difference images in each iteration (or at least, on the initial difference image) for a clearer definition of the region of interest footprint. This allows a more accurate determination of the motion estimation and the forwarded vector field to correct or update the motion compensator and/or adjust the input images (embolus or mask image). In one embodiment, the update module feeds the motion information into the algorithm of the image enhancer for initialization or as a constraint, etc. The image enhancer IE may be invoked in each iteration, or some (e.g., every k-th, k>2) or may be invoked on user demand only.

In one embodiment the motion compensator operates in co-operation with a landmark identifier on which the motion compensation is based. As mentioned above suitable landmarks are the footprint of the embolus itself or of the catheter tip or other (preferably salient) feature of the catheter or of a tool or object resident in the field of view of the imager during the acquisition of the fluoroscopic imagery. Preferably, the motion of the landmark is "translatable" into a motion of the ROI where the embolization occurs. It will be appreciated that the contrast conferring agent as used herein (for instance, the embolization agent) is assumed to be of higher viscosity than the contrast dye usually injected in cardio-interventions into blood vessels to confer contrast in traditional DSA settings.

Figure 2:
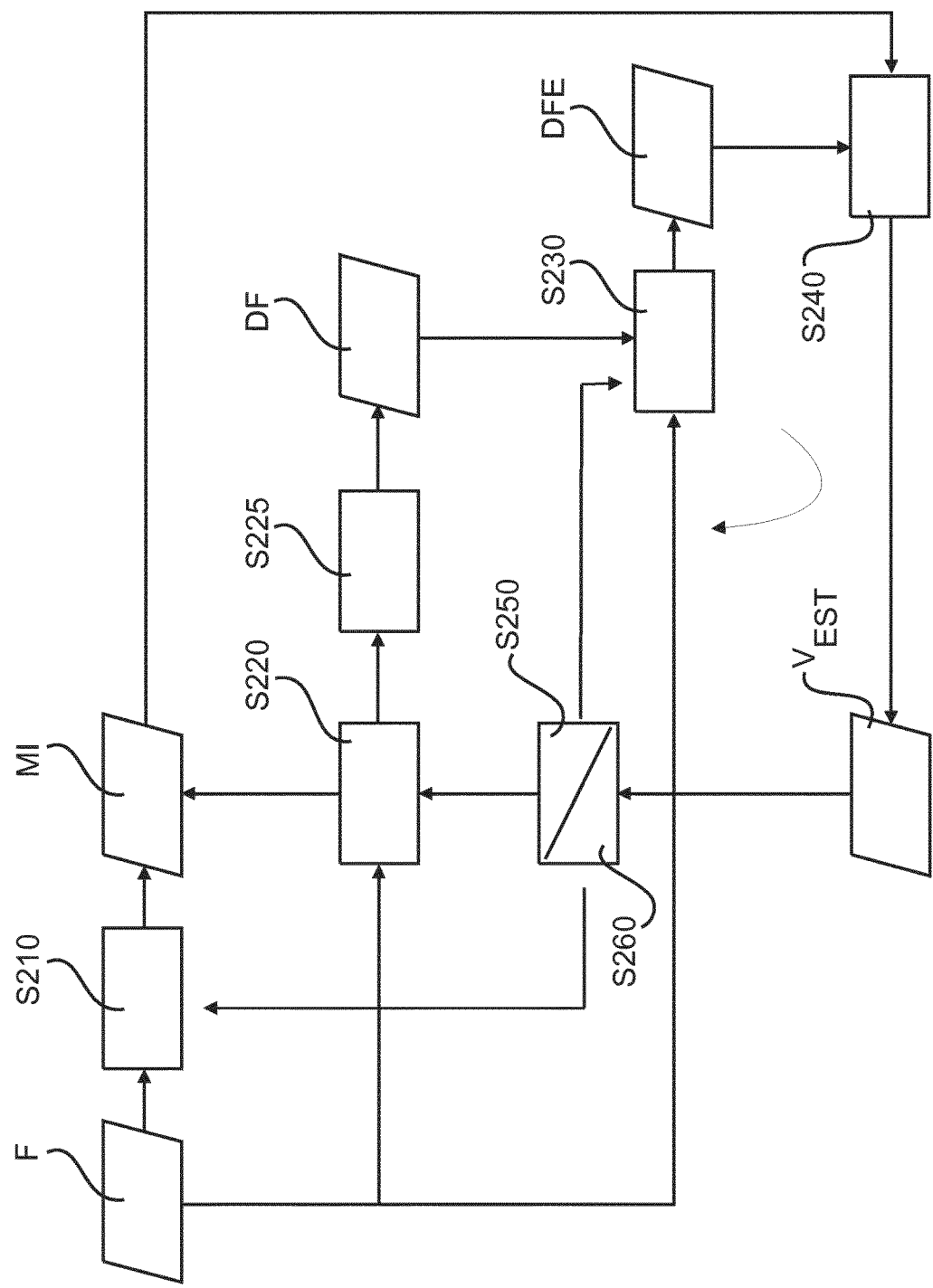
FIG. 2 shows a flow chart for an image processing method.

Reference is now made to the flow chart in FIG. 2 to explain in more detail the method underlying operation of the image processing system IPS briefly introduced above.

At step S210, an embolus image and a mask image are received. The mask image can be picked up from the stream of fluoroscopic imagery produced by the imager for instance, by grey value monitoring of the stream of frames. If the grey value is above or near the grey value of the local background, it is concluded that no embolization agent is present at the acquisition of the respective fluoroscopic frame and this frame is then considered to be a mask image for present purposes. Although the procedure will now be explained with reference to a particular mask image, the present method is applicable to embodiments where the mask image is changed. In other words, the following steps to be described in more detail below may be repeated every time the mask image is updated. It should also become clear from the above that the embolus frame itself is updated as more recent frames are received at input port IN. An imaging run usually covers at least in parts the process of depositing the embolization agent at the region of interest, with each frame capturing an up-to-date image of the evolving embolus as it grows and/or changes shape during the procedure. In one embodiment, step S210 includes buffering one or more mask images for the later computing of the difference image DF. In its simplest version, this can be implemented as the selection of any n-th (automatically or user selected) frame of the imaging run. In one embodiment, the mask image is chosen as the latest frame acquired before embolization start. In more refined versions, re-masking can occur, and the mask might change on demand or automatically along the course of the intervention.

At step S220 the mask image and the current embolus image are registered onto each other to compensate for a motion or change that may have occurred during the two acquisitions. This is based in one embodiment on the tracked landmark across the two frames.

At step S225 the two images so registered are subtracted from each other, more particularly the mask image is subtracted from the embolus image. Before the subtraction is performed, the motion-compensating transform (as learned in step S220) is applied to one of those frames, for instance to the mask image, or the transform may be applied instead to the embolus image. The transform can either be rigid or elastic.

The difference image DF computed at step S225 is then forwarded to step S230 where the image portion representative of the embolus (or of the associated landmark) is enhanced by a suitable filter operation. This step aims at enhancing and possibly isolating the embolic area in the current difference image as per step S225. In its simplest version, this can be a replica of the difference image. But it can be much more elaborate. The embolic material and area properties can be taken into account to filter the difference image and enhance this area. All sorts of level windowing and spatial filtering (such as differential or morphological filtering) can be used, each or any combination thereof being envisaged herein in different embodiments. Fuzzy or hard connected components (e.g., n-connected, e.g. n=4 or n=8 or any n being any other suitable number) can be used to isolate or at least identify the embolic area footprint if sufficiently distinct from the other artefact-originated image objects. Identification or isolation is by creating a feature or probability map that assigns a score to each pixel: for instance, as score '1' may be taken to encode that the feature is detected at the respective pixel whereas '0' indicates the respective pixel is a background pixel. Any value in between 0 and 1 can then be seen as a probability for the respective pixel to represent part of the embolus footprint.

The so enhanced difference image DFE is then forwarded to step S240 where a motion estimation is performed, but this time based on the enhanced difference image DFE (in particular the ROI or landmark footprint recorded therein and now enhanced) and either the mask image or more preferably the current image frame F or a newly received frame F or newly received mask image. The motion estimation at step S240 results in a motion descriptor, for instance, a vector field $V_{EST}$ but may be as simple as a single vector to describe the estimated motion. For the motion estimation step at step S240 any rigid and/or non-rigid motion estimation algorithms or optical flow techniques may be used. The motion descriptor (e.g., motion vector field $V_{EST}$) is then passed on to one or more update steps S250, S260.

The update step S250, S260 implements the iterative nature of the proposed subtraction imaging method as indicated by the curved arrow in flow chart FIG. 2. A number of different embodiments are envisaged in update step S250.

For instance, in one embodiment the motion information $V_{EST}$ is fed at step S250 into the motion compensator step S220. The motion information encoded in the motion descriptor can now be used by the motion compensator for future computations. In other words, if step S225 is performed on a newly received pair of embolus and/or mask frames, a more accurate registration can be achieved because now the motion information for the registration has been obtained from the previous difference image and more preferably from the enhanced image, and each is expected to more accurately reflect the motion that occurred and gives a more accurate and up-to-date "clue" on the location, shape and extent of the embolus as per its footprint. Also, the motion descriptor can be used to inform the motion compensation algorithm at step S220 about the motion that has already occurred and this dynamic knowledge can then be incorporated in the motion compensation algorithm.

The motion information may be thought of as a prior-knowledge "model" to be used for the motion compensation. If this (motion) model is consistent with the image data, one updates the motion compensation, if not, one rejects the motion compensation. Acceptance and rejection may be fuzzified for intermediate values during the iterations. An exemplary embodiment for this is Kalman filtering. Using said motion information $V_{EST}$ by back-feeding same into the motion compensation step S220 allows preventing the motion compensation to produce results that violate established laws of nature such as mass conservation laws etc. For instance, an isolated, dark pixel cannot be part of the embolus, nor can a larger dark patch, which is not connected to the main body of the embolus footprint. Another example is a patch that is "dark" in one frame, but disappears in another frame. For a similar purpose, and in addition or instead of step S220, the motion information VEST may be fed into a filter or other image enhancement algorithm underlying the image enhancement step S230.

In addition, or instead of updating the respective algorithms at step 220 or at step S230, it is envisaged herein to use in step S260 the motion knowledge gained from the enhanced difference image (or in some cases direct from the difference image from the previous iteration) to remove motion artifacts in a (current or new) embolus image and/or mask image before said embolus image and/or mask image is fed into the motion compensation step or registration step at step S220. For instance, the motion descriptor is used to transform (e.g., shift) the current or a subsequent embolus frame or the current mask frame or a newly received mask frame (if such a mask-update is requested by the user for instance) accordingly so as to perform a "pre-registration" before the two frames are then registered at step S220.

In one embodiment the previously computed motion field can also be used to predict, based on the probability map, the location and extent/shape of the embolus footprint for the follow up iteration given the location and shape of the embolus footprint as computed in the earlier iteration. This motion prediction information can then be used in a subsequent operation of registration step S220 and/or the enhancement step S230 when performing the filtering (e.g. Kalman) or contrast enhancing operation. In one embodiment, the probability or feature map can be constructed or updated from the estimated vector fields to capture the dynamics of the embolus as it expands during the deposition of the embolization agent at the region of interest. The probability map may be used to control operation of the one or more filter or other image processing algorithms (e.g., Kalman or other any filter algorithm that accepts previous result(s) as input data, either on their own, or in addition to current data) at enhancement step S230 or registration step S220. Again, use is made here of the slow evolution of the embolus and the manner in which the embolus is deposited. The later can be expected in most circumstances to be largely predictable due to the slow dispersion of the embolization material at the region of interest and a relatively constant flow rate that is unlikely to change during the time period between the frame acquisitions. Any combination of the described embodiments for the update step S250 is also envisaged herein.

In sum, the method can see to embody different iterative aspects: for one, a current difference image (based on a current embolus frame and current mask frame) may be iteratively improved by using the additional, more accurate motion information as per step S240 gathered from a previous difference image. The number of iteration runs can be pre-defined, or each re-run is specifically requested by the user (e.g., after visual inspection of output difference image if it proves unsatisfactory). In addition, or instead, the method iteratively improves upon the motion information available at the image registration or motion compensation step at S220 or at the image enhancement step at S230. This information can then be used for follow up subtractions at step S225 or image enhancements at step S230 for a next pair of embolus and mask frames. Instead of, or in in addition to each of these iterative actions, the more accurate or updated motion information may be used to modify or adjust at step S260 the input images (the current frame pair or a subsequent frame pair) by removal of artifacts or by adjusting S260 their relative positions in a common coordinate system before passing the pair of frames to the image registration/tracking step at step S220.

Because the proposed system and method relies on the "stratification" of embolization material footprint in the image (that remains in place as opposed to the "fleeting" contrast agent footprint as per traditional DSA), it is easy to show that the difference images will "converge" or "latch on" any object having this property. For instance, introducing an instrument or tool after the imaging run start and then subsequently injecting contrast agent will have the effect that the difference image will be converged for the projection footprint of the instrument and not on the contrast agent. In a usual DSA, one would experience a reverse situation.

The image processing module IPS may be arranged as a software module or routine with a suitable interface IN to read in the fluoro stream F and may be run on a general purpose computing unit or a dedicated computing unit. For instance, processor IPS may be executed on a workstation or console CC of the imaging system 100. The image processing module IPS with some or all of its components may be resident on the executive agency (such as a general purpose computer, workstation or console) or may be accessed remotely/centrally by the executive agency via a suitable communication network in a distributed architecture. The components may be programmed in a suitable scientific computing platform such as Matlab® or Simulink® and then translated into C++ or C routines maintained in a library and linked when called on by the executive agency such as the general purpose computer, workstation or console. Preferably the machine implementation and or programming of the various step of the IPS algorithm are arranged so as to ensure real-time capability.

In one embodiment, the components of the image processing module IPS may be arranged as dedicated FPGAs (field-programmable gate array) or similar standalone chips.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
    a processor configured to perform iterative processing of a series of sequential projection images in which each iteration processes two projection images of the series of sequential projection images including i) an embolus projection image acquired of a region of interest (ROI) in a specimen whilst an embolus is present at or around said ROI and ii) a mask projection image acquired at a different instant than the embolus projection image when less or none of the embolus is present, an amount of said embolus capable of building up over time, the image processing system applying, in each iteration:
        ROI focused motion compensation that operates to register the mask projection image and the embolus projection image to motion compensate for a motion of the ROI;
        a subtractor configured to subtract, after said image registration, the mask projection image from the embolus projection image to obtain a difference image;
        an image enhancer configured to filter the difference image for an image portion that represents the ROI;
        a motion estimator configured to establish motion information in respect of a motion of the ROI, based on the filtered difference image and based on i) the embolus projection image or ii) the mask projection image; and
        an update module configured to provide said estimated motion information from a current iteration of the iterative processing of the series of sequential projection images to a next iteration of the iterative processing of the series of sequential projection images including inputting said estimated motion information into the image enhancer and/or adjusting at least one of: an embolus projection image or a mask projection image provided to the ROI focused motion compensation in the next iteration of the iterative processing of the series of sequential projection images.

2. The image processing system according to claim 1, wherein the ROI focused motion compensation includes identifying in the images a landmark that corresponds to the ROI or to a device resident in the specimen during imaging, in particular the device operative to deposit said substance.

3. The image processing system according to claim 1, wherein the ROI is defined by the location and/or shape of the currently deposited substance.

4. A non-transitory computer readable medium comprising instructions executable by a computer to perform an image processing method comprising the steps of:
    a) receiving i) a projection image acquired of a region of interest, ROI, in a specimen whilst a substance is present at or around said ROI and ii) a mask image, the mask projection image acquired at a different instant than the projection image when less of said substance is present, an amount of said substance capable of building up over time;
    b) registering the mask image and the projection image to motion compensate for a motion of the ROI;
    c) subtracting, after said image registration, the mask image from the projection image to obtain a difference image;
    d) enhancing the difference image for an image portion that represents the ROI;
    e) estimating a motion of the ROI based on the enhanced difference image and based on i) the projection image or ii) the mask image; and
    f) using the estimated motion information as input for a subsequent iteration of the method.

5. The image processing method of claim 4, wherein step f) comprises:
    inputting said estimated motion into the registering step or the enhancing step.

6. The image processing method of claim 5, wherein step f) comprises:
    adjusting a new embolus image and/or mask image to remove motion artifacts before said embolus image and/or mask image is fed into the registering step.

7. An image processing system, comprising:
    at least one computer processor configured to receive i) a projection image acquired of a region of interest, ROI, in a specimen whilst a substance is present at or around said ROI and ii) a mask image acquired at a different instant than the projection image when less of said substance is present, an amount of said substance capable of building up over time;
    the at least one computer processor programmed to:
        register the mask image and the projection image to motion compensate for a motion of the ROI;
        subtract, after said image registration, the mask image from the projection image to obtain a difference image;
        filter the difference image for an image portion that represents the ROI;
        establish motion information in respect of a motion of only the ROI, based on the filtered difference image and based on i) the projection image or ii) the mask image; and
        adjust at least one of: a subsequent projection image or a subsequent mask image.

8. The image processing system according to claim 7, wherein the at least one computer processor is further programmed to:
    identify in the images a landmark that corresponds to the ROI or to the device operative to deposit said substance.

9. The image processing system according to claim 7, wherein the ROI is defined by the location and/or shape of the currently deposited substance.

10. The image processing system according to claim 1, wherein the substance is a blob of embolization agent.

* * * * *